United States Patent [19]

Chao

[11] Patent Number: 4,812,595
[45] Date of Patent: Mar. 14, 1989

[54] ALKYLATION OF AMINE COMPOUNDS

[75] Inventor: Kuo-Hua Chao, Houston, Tex.

[73] Assignee: Shell Oil Company, Houston, Tex.

[21] Appl. No.: 111,953

[22] Filed: Oct. 23, 1987

[51] Int. Cl.[4] .................. C07C 85/00; C07C 85/24
[52] U.S. Cl. .................................. 564/463; 564/470;
564/467
[58] Field of Search .................. 564/463, 470, 469

[56] References Cited

U.S. PATENT DOCUMENTS 4,430,513  2/1924  Homeier ................ 564/470 X
4,562,291  12/1985  Wilson et al. ............. 564/463

Primary Examiner—Howard T. Mars

[57] ABSTRACT

Alkylamines are self-alkylated to longer carbon chain alkylamines using a catalyst mixture comprising a quaternary ammonium halide in combination with ruthenium carbonyl.

12 Claims, No Drawings

ALKYLATION OF AMINE COMPOUNDS

FIELD OF THE INVENTION

The present invention relates to the catalytic synthesis of longer chain alkylamines by the oligomerization of self-alkylation of mono-, di- and trialkylamines.

BACKGROUND OF THE INVENTION

The common method of alkylating organic compounds is by using alkylating agents such as olefins or alkylhalides in the presence of a Friedel Crafts catalyst. When amines are used as alkylating agents with Friedel Crafts catalysts, the alkylation reaction is severely inhibited by the fact that the amine poisons the catalyst by the formation of an acid-base compound.

U.S. Pat. No. 4,430,513, issued Feb. 7, 1984, discloses one method in which alkylamines can satisfactorily be used as alkylating agents. Specifically, this patent teaches the self-alkylation of alkylamine compounds which contain at least two alkyl substituents containing from about 2 to 6 carbon atoms. The alkylamine compounds are alkylated in the presence of a rhodium or cobalt carbonyl or a rhodium or cobalt compound which is capable of forming a carbonyl under alkylation conditions.

U.S. Pat. No. 4,562,291, issued Dec. 31, 1985, discloses the self-alkylation of mono-, di- and trialkylamines using a catalyst mixture comprising a tetrafluoroborate salt and a ruthenium, an osmium or an iridium-containing compound.

In co-pending U.S. Application Ser. No. 940,385, filed Dec. 10, 1986, is discussed the use of a catalyst mixture comprising aluminum chloride in combination with cobalt and/or ruthenium carbonyl.

In co-pending U.S. Application Ser. No. 17,501, filed Feb. 24, 1987, is discussed the use of a catalyst mixture comprising Zr/Hf/Ti metallocenes in combination with cobalt and/or ruthenium carbonyl.

The oligomerized alkylamines prepared by the process of the instant invention are useful for preparing detergent products and disinfectant products.

SUMMARY OF THE INVENTION

The present invention involves a process for the catalytic synthesis of long chain alkylamines. Specifically, mono-, di- or trialkylamines are oligomerized or self-alkylated to form longer chain alkylamines by contacting the mono-, di- and/or trialkylamines with a catalyst mixture comprising a quaternary ammonium halide and a ruthenium carbonyl or ruthenium-containing salt(s) capable of forming a carbonyl under alkylation conditions. The mole ratio of cobalt and/or ruthenium carbonyl to quaternary ammonium halide typically ranges from about 1:1 to about 1:100. A particular advantage of the instant invention is that it can be used to convert alkylamines to their mono-alkylated amine products in high yield. Selectivities of the instant catalyst combinations result in the product amines being predominantly (i.e., greater than about 50%) the mono-alkylates. This can result in simpler product mixes with concomitant lower separation costs.

DETAILED DESCRIPTION OF THE INVENTION

The present invention provides a process for synthesizing long chain alkylamines by self-alkylation or oligomerization of shorter chain alkylamines. Any typical alkylamine can be oligomerized in accordance with the present invention. The invention is particularly suitable for alkylating trialkylamines. Oligomerization produces a mixture of various longer chain alkylamines. In a preferred embodiment, the instant process converts an amine predominately to its next higher homologue i.e., a mono-alkylated amine. For example, triethylamine is converted predominately to butyldiethylamine with significant amounts of butylethylamine also being produced. Thus, in a preferred embodiment amines of the general formula

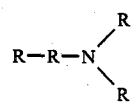

are prepared from amines of the general formula

wherein R is alkyl, preferably $C_1$–$C_6$ alkyl.

The reaction is run in the presence of a catalyst mixture comprising a quaternary ammonium halide and a ruthenium carbonyl or a ruthenium-containing compound which is capable of being converted to carbonyls under alkylation conditions. The mole ratio of ruthenium carbonyl to quaternary ammonium halide in the catalyst mixture will range from about 1:1 to about 1:100, more preferably from about 1:1 to about 1:20.

The quaternary ammonium halides useful as co-catalysts have the general formula $R_1R^2R^3R^4N^+X^-$ wherein X is halide, e.g., chloride, bromide, iodide or fluoride and the R groups may be different or alike and may be substituted or unsubstituted branched-chain or unbranched, saturated or unsaturated. They may be alkyl, aralkyl, aryl or alkaryl. Two or three of the R groups may be formed into heterocyclic ring compounds to provide, for example, pyridinium or quinolinium halides. Any quaternary ammonium halide that is soluble in the reaction mixture is suitable, which solubility can be determined by routine experimentation. Preferred quaternary ammonium halides are the tetraalkylammonium halides wherein the alkyl group has from 1 to about 20, preferably from 1 to about 10 carbon atoms.

Generally, carbon monoxide is added to the reaction mixture. While carbon monoxide is not absolutely needed when the carbonyls are used in the reaction mixture, its presence adds to the stability of the catalyst mixture. When ruthenium compounds are used, carbon monoxide is added to the reaction mixture to convert the compounds to the carbonyls. The presence of hydrogen is not required in the reaction mixture. Its presence has no adverse effects and the use of syngas to provide the reaction mixture with carbon monoxide will also provide hydrogen.

The oligomerization is a liquid phase reaction. It is preferably carried out in the presence of a solvent, preferably an amine solvent. Most preferably the solvent is an aliphatic amine. Preferably the reactant amines are used as the reaction solvents. Other solvents such as alcohols, ethers, aromatics or paraffins can be used, but are less desirable.

The oligomerization reaction is typically carried out at a temperature range of from about 50° C. to about 300° C., more preferably from about 150° C. to about 250° C. Procedures will typically run from about 1 atmosphere to about 500 atmospheres, more preferably from about 1 to about 300 atmospheres and more preferably from about 20 to about 100 atmospheres.

The process of the instant invention may be accomplished in either a batch or continuous type operation. For example, when a batch type operation is to be employed, a quantity of the catalyst and amine compound along with an organic solvent, if one is to be used, will be placed in a pressure-resistant apparatus such as an autoclave of the stirring, mixing or rotating type. Following the addition of the catalyst and starting material, the apparatus is sealed, flushed with an inert gas such as nitrogen, and pressurized to the desired operating pressure with carbon monoxide and optionally hydrogen. Upon reaching the desired operating pressure, the apparatus is then heated to a predetermined operating temperature and maintained thereat for the desired residence time which may range from about 0.5 up to about 20 hours or more in duration. Upon completion of the desired residence time, heating is discontinued and after the apparatus and contents thereof have returned to room temperature, the excess pressure is discharged, the apparatus is opened, and the reaction mixture is recovered therefrom. After separation of the product mix from the catalyst, the former may then be subjected to conventional means of separating the components of said mix, said means including fractional distillation, fractional crystallization, etc.

It is also contemplated within the scope of this invention that the alkylation of the alkylamine compound may be accomplished in a continuous manner of operation. When such a type of operation is employed, the starting material comprising the alkylamine is continuously charged to an apparatus which is maintained at the proper operating conditions of temperature and pressure. In addition, the catalyst which is to be employed as well as any solvent is also continuously charged to the reaction apparatus either through separate lines or, if so desired, the components of the reaction mixture may be admixed prior to entry into the reaction apparatus and the resulting mixture charged thereto in a single stream. After passage through the apparatus for a predetermined period of time, the reactor effluent is continuously withdrawn and subjected to conventional means of separation whereby the product mix is separated from the catalyst and any unreacted starting material that is to be recycled to the reaction apparatus to form a portion of the feedstock, while the product mix is subjected to further distillation to recover the various components of said mix.

The process of this invention is further described by the following illustrative embodiments which are provided for illustration and are not to be construed as limiting the invention.

EXAMPLE 1

To a 100 cc stainless steel screw top autoclave was added 29.0 grams of triethylamine, 44.5 mg (0.183 mmol) of tetraethylammonium iodide and 117 mg (0.183 mmol) of triruthenium dodecacarbonyl, the molar ratio of triethylamine to ruthenium carbonyl to tetraethylammonium iodide being 1570:1:1. The autoclave was sealed under inert atmosphere and flushed with carbon monoxide, following which the autoclave was pressurized to 100 psi with carbon monoxide. Thereafter, the autoclave was heated to a temperature of 220° C. and maintained there for a period of 6 hours. At the end of this period, heating was discontinued and the autoclave was allowed to return to room temperature. The excess pressure was discharged, the autoclave was opened, and the reaction product was recovered. The product was analyzed by means of gas liquid chromatography and mass spectroscopy. This analysis determined that there had been a 65.0% w conversion of the triethylamine and that the triethylamine which had been converted to higher alkylamines (50%) was converted with the selectivity shown in Table I below.

TABLE I

| Alkylated Product | Weight Percent |
|---|---|
| butyldiethylamine | 54.0 |
| butylethylamine | 30.3 |
| ethyldibutylamine | 11.6 |
| ethylhexylamine | 4.0 |

EXAMPLE 2

The above experiment was repeated using tetrahexylammonium bromide instead tetraethylammonium iodide. Analysis determined that there had been a 65% w conversion of the triethylamine and that the triethylamine which had been converted to higher alkylamines (50%) was converted with the selectivity shown in Table II below.

TABLE II

| Alkylated Product | Weight Percent |
|---|---|
| butyldiethylamine | 54.5 |
| butylethylamine | 29.3 |
| ethyldibutylamine | 10.6 |
| ethylhexylamine | 5.6 |

COMPARATIVE EXAMPLE A

Example 1 above was repeated in a similar fashion except that as catalyst only triruthenium dodecacarbonyl as used. The mole ratio of $(CH_3CH_2)_3N:Ru_3(CO)_{12}$ was 1570:1. Analysis determined that there had only been a 2% w conversion of the triethylamine and that the triethylamine which had been converted to higher alkylamines (50%) was converted with the following selectivities: butyldiethylamine-92% w and hexyldiethylamine-7% w.

I claim:

1. A process for the oligomerization of alkylamines to produce longer carbon chain alkylamines which process comprises contacting said alkylamines at a temperature of from about 50° C. to about 300° C. with a catalyst mixture comprising a quaternary ammonium halide and a component selected from a ruthenium carbonyl, a ruthenium-containing compound capable of being converted to a carbonyl under oligomerization conditions and mixtures thereof.

2. The process of claim 1 wherein the ruthenium carbonyl is triruthenium dodecacarbonyl.

3. The process of claims 1 or 2 wherein the mole ratio of ruthenium carbonyl to quaternary ammonium halide ranges from about 1:1 to about 1:100.

4. The process of claims 1 or 2 wherein carbon monoxide is added to the oligomerization mixture.

5. The process of claims 1 or 2 wherein the temperature ranges from about 175° C. to about 250° C.

6. The process of claims 1 or 2 wherein the alkylamine is triethylamine and the longer carbon chain product amine consists predominately of butyldiethylamine.

7. The process of claims 1 or 2 wherein the longer carbon chain amine consists predominately of monoalkylated amine.

8. The process of claims 1 or 2 wherein the pressure is maintained between about 1 and about 500 atmospheres.

9. The process of claims 1 or 2 wherein the quaternary ammonium halide is a tetraalkylammonium halide.

10. The process of claim 9 wherein the alkyl has from 1 to about 10 carbon atoms.

11. A process for preparing butyldiethylamine which process comprises oligomerizing triethylamine by contacting said triethylamine at a temperature of from about 175° C. to about 250° C. with a catalyst mixture comprising a quaternary ammonium halide and a component selected from a ruthenium carbonyl, a ruthenium-containing compound capable of being converted to a carbonyl under oligomerization conditions and mixtures thereof wherein the ratio of ruthenium carbonyl to quaternary ammonium halide ranges from about 1:1 to about 1:100.

12. The process of claim 11 wherein the quaternary ammonium halide is a tetra-alkylammonium halide wherein the alkyl group has from 1 to about 10 carbon atoms.

* * * * *